United States Patent [19]
Bogart et al.

[11] Patent Number: 5,494,801
[45] Date of Patent: Feb. 27, 1996

[54] MICROORGANISM ANTIGEN EXTRACTION METHODS

[75] Inventors: Gregory R. Bogart, Berthoud; Robert J. Bilodeau, Arvada; Rachel M. Ostroff, Westminster; Jeffrey W. Steaffens, Louisville, all of Colo.

[73] Assignee: Biostar, Inc., Boulder, Colo.

[21] Appl. No.: 162,401

[22] Filed: Dec. 3, 1993

[51] Int. Cl.$^6$ .................................................. G01N 33/569
[52] U.S. Cl. ..................... 435/7.34; 435/7.32; 435/7.92; 435/7.1; 435/7.95; 435/29; 435/961; 435/962; 435/975; 436/518; 436/174; 436/175; 436/808; 422/61
[58] Field of Search ............................ 435/6, 7.32, 7.34, 435/961, 962, 975, 7.92, 7.95, 29, 259, 885, 243.4, 7.1; 436/518, 174, 175, 808; 422/61

[56] References Cited

U.S. PATENT DOCUMENTS

| | | | |
|---|---|---|---|
| Re. 33,850 | 3/1992 | Snyder et al. | 435/7.34 |
| 4,673,639 | 6/1987 | Slifkin | 435/36 |
| 4,851,337 | 7/1989 | Berke | 435/29 |
| 4,978,632 | 12/1990 | Mach et al. | 435/7.36 |
| 5,061,970 | 10/1991 | Elting et al. | 530/402 |
| 5,132,205 | 7/1992 | Pronovost et al. | 435/5 |

FOREIGN PATENT DOCUMENTS

| | | | |
|---|---|---|---|
| 556521 | 8/1993 | European Pat. Off. | C12N 1/06 |
| 9315217 | 8/1993 | WIPO . | |

OTHER PUBLICATIONS

Van Nostrand Reinhold Encyclopedia of Chemistry, 4th Edition, Considin. ed., (Van Nostrand Reinhold Co. N.Y., 1984). p. 483.

1992 Sigma Chemical Company catalog, pp. 911 and 2147 (St. Louis, Mo.).

Edwin H. Lennette "Manual of Clinical Biology" *American Society for Microbiology* (1980) 3rd Ed. 95–96.

P. W. Ross, "Group–B Streptococcus–Profile of an Organism" *J. Med. Micro.* (1984) 18:139–166.

Primary Examiner—Michael P. Woodward
Assistant Examiner—Jeffrey Stucker
Attorney, Agent, or Firm—Lyon & Lyon

[57] ABSTRACT

Method for extracting an antigen from a micro-organism organism of the genus streptococcus contained in a sample including the steps of contacting the sample with reagents which generate hyponitrous acid, further contacting the sample with a base, or contacting the sample with hypochlorite, and neutralizing the sample.

44 Claims, 1 Drawing Sheet

MICROORGANISM ANTIGEN EXTRACTION METHODS

FIELD OF THE INVENTION

The present invention relates to materials and methods for extraction of antigens from micro organisms.

BACKGROUND OF THE INVENTION

Several techniques for extraction of antigens from micro organisms are well known to those skilled in the art. Cellular antigens such as carbohydrates, proteins, lipoproteins, lipopolysaccharides, polysaccharides, nucleic acids, carbohydrates complexed with proteins, lipids, and others have been extracted by a variety of chemical or mechanical means. Such extraction techniques include boiling, autoclaving, detergent extraction, acid extraction, digestion with hot formamide, nitrous acid extraction, sonication or other mechanical disruption, phenol/chloroform extraction, or digestion by enzymes. If an antigen is to be used in an immunological assay it is important that the extraction protocol preserve the binding characteristics of that antigen.

Nitrous acid is a chemical extraction technique (Manual of Clinical Microbiology, Third Edition, Edwin H. Lennette, Albert Balows, William J. Havsler, Jr., and Joseph P. Traunt, Editors, American Society for Microbiology, Washington, D.C. (1980)). The method, traditionally, involves mixing two liquid reagents, an acid and a nitrite salt solution. This mixture generates a nitrous acid intermediate in solution. This nitrous solution is generally neutralized prior to subsequent steps. Assay kits based on this method include three separate reagent bottles designed to deliver a predetermined volume, i.e., a number of drops, of each reagent to a sample tube.

Variations of this technique have been described. For example, Sand et al. (patent application, WO93/15217), describes an extraction of Group A or B Streptococci with two dried and one liquid reagent. The sodium nitrite and Tris base awe dried onto separate filter pads and an excess volume of acetic acid is added to reconstitute first the $NaNO_2$, and then (after an extraction period) the Tris base which neutralizes the solution.

U.S. Pat. No. 4,851,337, describes another modification of the nitrous acid extraction protocol in which one vessel contains a polymeric acid and one contains a nitrite solution. While not reducing the number of reagents, this method provides pre-measured solutions that can be quickly mixed to allow antigen extraction. The end-user is not required to measure a specified number of reagent drops to the sample tube. In this method, the nitrite solution is transferred to a tube containing dried polymeric acid, mixed, and a sample swab added. After an incubation period, the solution is neutralized by the addition of a reagent from another tube.

U.S. Pat. No. 4,673,639, describes another modification of the nitrous acid extraction protocol, using microtubes containing two dried reagents in discrete zones of the tube. Reagents are reconstituted and activated by the addition of water and the sample containing swab. Reagents are held within the tube by inert binders or carriers such as dextran, polyacrylamide, polyacrylic acid, polyvinyl alcohol, PEG, PEO, PVP, guar gum, caboxymethylcellulose, hydroxyethyl cellulose, methyl cellulose, algin, carrageenan, and xanthan gum.

Extraction of antigens is an important step in the identification of micro organisms that are related to various disease states, such as Group A Streptococcus and Group B Streptococcus (GBS). Once the organism's antigens are extracted, they may be used for isolation and purification of a specific material for subsequent production of antibodies or vaccines or a variety of other uses. The extracted antigens which are specific to a given organism, may be used for the identification of the that organism from a test sample. The test sample may be any clinically relevant sample, such as serum, blood, urine, plasma, sputum, semen, throat swabs, vaginal swabs, and various secretions or other fluids. Of particular interest is the use of an immunoassay technique for the identification of a specific antigen for the diagnosis of a specific infection.

There are a variety of immunoassay techniques available. All rely on the ability of an antibody and its corresponding antigen to specifically interact. Latex agglutination relies on particle aggregation, colored or white, for the detection of a specific interaction. Antibodies may be labeled with radioactive, enzymatic, metallic particles, fluorescent, chemilluminescent, or a variety of other labels to produce an interpretable signal. In a classic form of immunoassay, an enzyme labeled antibody is used to convert a colorless substrate to a colored product which may be measured spectrophotometrically. Another immunoassay technique involves optical immunoassays. These techniques rely on the unique interactions of thin films with light to measure a mass change on the thin films and are described in U.S. Ser. No. 08/075,952, filed Jun. 11, 1993, entitled "Devices and Methods For Detection" is incorporated by reference herein, including drawings.

SUMMARY OF THE INVENTION

This invention features methods and kits for the extraction and detection of antigens from micro-organisms using an improved extraction procedure combining a nitrous acid reagent with base or hypochlorite, or relying on hypochlorite alone. Cellular antigens such as carbohydrates, proteins, lipoproteins, lipopolysaccharides, polysaccharides, nucleic acids, carbohydrates complexed with proteins, lipids, and others are examples of the types of materials which may be extracted. The methods of the present invention focus on improving sample extraction so as to increase antigen availability. The present invention embodies rapid, simple extraction protocols, that obviate the need to remove extraction reagents prior to identification, do not damage the material to be identified, and allow for a greater amount of antigen to be made accessible to binding reagents such as antibodies. These methods achieve such efficient extraction of antigens so as to enable the identification of the micro organism in a sample even when present at low concentrations.

The present invention also provides methods for the detection of extracted antigens. Detection is preferably made by an immunoassay technique, and most preferably by optical immunoassays that allow for rapid, sensitive, and accurate diagnosis of disease-causing micro organisms. In particular, the methods are useful for extraction and identification of streptococci from sample swabs. And more specifically for the extraction and identification of Group B Streptococci.

GBS is the leading cause of neonatal and maternal morbidity and mortality. The neonate may develop early-onset disease between birth and the neonate's first week. The disease is characterized by respiratory distress, sepsis, and shock. There are between 1.9 to 3.7 cases per 1,000 live births in the U.S. alone, with a mortality rate of 26% to 50%; and 30% of the infected infants will develop meningitis. Of the latter group, 50% will suffer permanent neurological damage. Infection with GBS is estimated to cost the U.S. alone over $500 million per year in health care.

GBS also causes a late onset disease that occurs within the first 3 months following birth. The illnesses in these cases are characterized by central nervous system disorders, meningitis, and bacteremia. There is an approximately 20% mortality rate for infants with these diseases. Direct correlation of maternal cervical/vaginal carriage of GBS and infant infection has been demonstrated. Treatment of the mother, pre-delivery, greatly improves the neonatal outcome and can eliminate the vertical transmission of GBS.

An increase in the antigen extraction efficiency of Group B *Streptococcus* (GBS), *Streptococcus agalactiae,* is critical to identification of this organism at the clinical sensitivity required. GBS group specific antigen is covalently linked to the cell wall peptidoglycan and actually crosses the entire cell wall making extraction of this antigen more difficult than similar antigens from other organisms (J. Med. Micro., 18, 139–166, 1984). Antigens from Group G, Group F, and Group A *Streptococcus* are also extracted by these methods.

The invention features extraction reagents which are also effective mucolytic agents. These extraction reagents facilitate antigen extraction by a direct cell disruption mechanism and by lysing the sample's mucus. Lysing the mucus exposes cells to the extraction reagent and reduces non-specific binding.

In one method, applicant has determined that an incubation step in base immediately following nitrous acid extraction increases antigen available for an immunoassay technique. In a second method, sodium hypochlorite is used for extraction and again facilitates the release of antigen for immunoassay techniques. The hypochlorite step can be followed by a nitrous acid extraction step.

The extraction methods of this invention are well suited for preparation of samples for use in optical immunoassays. The invention also features methods and kits for detection of antigens extracted from micro organisms based on the combination of these extraction techniques and optical immunoassays. Three techniques are preferred. One relies on the interaction of white light with thin films to produce a visible interference effect, one on the interaction of ellipsometrically polarized light to produce a quantifiable signal, and one on the interaction of linearly polarized light with the thin films to produce a change in light intensity.

Thus, in a first aspect, the invention features a method for extraction of an antigen from a micro organism contained in a sample by contacting the sample with reagents which generate nitrous acid for a period of time sufficient to allow the nitrous acid to extract the antigen, contacting the sample with base for a period of time sufficient to increase the exposure of the antigen, and finally neutralizing the sample.

By "reagents which generate nitrous acid" is meant the combination of sodium nitrite and acetic acid or other equivalent chemicals. Nitrous acid can be generated using other salts of nitrite. A liquid reagent may also be used to supply the sodium nitrite. A variety of other acids may be substituted for the acetic acid to react with the nitrite salt to form the nitrous reagent. Examples of other acids which can be used are: citric acid, sulfuric acid, hydrochloric acid, nitric acid, phosphoric acid or weak organic acids.

By "period of time sufficient to allow the nitrous acid to extract the antigen" is meant the incubation time required to release sufficient antigen from the micro organism to make it available for subsequent detection. This is typically in the range of instantaneous to 10 minutes.

By "base" is meant a reagent which is able to generate a solution of pH 12–14. A preferred reagent is sodium hydroxide, however, other reagents can be used, such as potassium hydroxide, ammonium hydroxide, or other strong bases.

By "period of time sufficient to increase the exposure of the antigen" is meant a time which further exposes the antigen to a greater extent than achieved by extraction with nitrous acid alone, such that the antigen is more exposed and more available for reaction with reagents used for detection, thus allowing for enhanced detection. Such enhanced detection allows detection either of lower amounts of antigen or provides a lower signal to noise ratio. This time period is typically in the range of 0.5 to 10 minutes.

By "neutralizing" is meant addition of a buffer system which achieves a final pH range of from 6.0 to 8.0. Examples of suitable buffer systems are MOPSO (0.2% TWEEN20™ detergent, 15% bovine serum, 0.5% PROCLIN300™ preservative, and 20 mM EGTA), TRIS, MOPS, and HEPES.

In a preferred embodiment, the reagents which generate nitrous acid consist of between 0.25M to 1.0M acetic acid and between 0.5 to 2.5M sodium nitrite, first contacting is for a period of time from 0.5 to 10 minutes, second contacting is for a period of time from 2 to 10 minutes, the base consists of between 2N to 6N NaOH and the neutralizing is with a buffer containing between 1.0 to 2.5M MOPSO at pH 6.0.

The sodium nitrite is preferably provided as a reagent previously dried into the extraction tube.

In a second aspect, the invention features a method for extracting antigen from a micro organism contained in a sample and for flysing mucous in the sample by contacting with reagents which generate nitrous acid for a period of time sufficient to allow the nitrous acid to extract the antigen, contacting the sample with base for a period of time sufficient to increase the exposure of the antigen and to lyse mucus in the sample, and finally neutralizing the sample.

By "lysing mucus" is meant effectively liberating the micro organism from the surrounding sample matrix and simultaneously reducing the non-specific binding that can be associated with the mucus in a sample.

In one embodiment, the sample is reacted with reagents which generate nitrous acid in the presence of a chelating agent and a disulfide bond reducing agent. In a preferred embodiment, the chelating agent is ethylenediaminetetraacetate (EDTA) or EGTA and the disulfide bond reducing agent is dithiothreitol. The concentration of EDTA or EGTA is preferably from 0.1 to 100 mM and the concentration of dithiothreitol (DTT) is preferably 0.1 to 100 mM. The EDTA or EGTA and DTT are optional, but provide improved performance with samples containing mucous.

In a third aspect, the invention features a method for extraction of an antigen from a micro organism contained in a sample by contacting the sample with hypochlorite and sodium nitrite for a period of time sufficient to extract sufficient antigen to make it available for subsequent detection, and neutralizing the sample. The method is equally effective when hypoclorite alone is used, without sodium nitrite.

By "hypochlorite" is meant a reagent as supplied in the form of an aqueous solution of sodium hypochlorite, although other hypochlorite salts can be substituted. Solutions of sodium hypochlorite containing up to 10% available hypochlorite are commercially available. Solid hypochlorite (containing 40% available hypochlorite) may be substituted for the commercially available solutions. A higher final concentration of hypochlorite could be provided with the solid material used to produce the liquid reagent simply by dissolving the solid in deionized water. It would also be possible to supply the hypochlorite reagent as a dried reagent in an extraction tube if desired. This method performs optimally when a greater than 6% aqueous solution of hypochlorite is used.

A useful period of time in this aspect is generally up to 30 minutes.

In preferred embodiment, the hypochlorite is between 0.1% to 10%, the sodium nitrite is between 0.5 to 2.5M, contacting is for a period of time from 2 to 30 minutes, and neutralizing is with a buffer containing 1.0 to 2.5M MOPSO at pH 7.0.

In a fourth aspect, the invention features a method for extracting an antigen from a micro organism contained in a sample by first contacting the sample with hypochlorite and sodium nitrate for a period of time sufficient to allow the hypochlorite to extract the antigen, second contacting the sample with reagents which generate nitrous acid for a period of time sufficient to increase the exposure of the antigen as described above, and neutralizing the sample.

By "period of time sufficient to allow the hypochlorite to extract the antigen" is meant the incubation time required to release antigen from the micro organism and make it available for subsequent detection.

By "reagents which generate nitrous acid" means incubation with acetic acid or a comparable acid and sodium nitrite as specified above.

By "period of time sufficient to increase the exposure of the antigen" is meant a period of time which further exposes the antigen to a greater extent than is achieved by extraction with hypochlorite and sodium nitrite, such that the antigen is more exposed and more available for reaction with reagents used for detection, thus allowing for enhanced detection. The hypochlorite/nitrous acid protocol allows for increased exposure of the antigen because the level of available hypochlorite can drop (although the stability of the hypochlorite solution at or below room temperature is excellent, at high temperatures hypochlorite decays slowly). Exposure to nitrous acid after this potential drop in hypochlorite levels ensures that the extraction process will continue. The order of addition for hypochlorite and acetic acid (used to generate nitrous acid) may be reversed while maintaining the same type of enhanced exposure of the antigen.

In a preferred embodiment, the hypochlorite is between 0.1% to 10%, the sodium nitrite is between 0.5 to 2.5M, first contacting is for a period of time from 2 to 30 minutes, and neutralizing is with a buffer containing 1.5M MOPSO at pH 7.0; the reagents which generate nitrous acid comprise acetic acid between 0.25 to 2.0 M and the second contacting is for a period of time from 0.5 to 30 minutes.

In a fifth aspect, the invention features a method for lysing mucous in a sample by contacting the sample with hypochlorite and sodium nitrite for a period of time sufficient to lyse mucus in the sample and neutralizing the sample. The method is equally effective when hypochlorite is used alone, without sodium nitrite.

This mucolytic effect of the hypochlorite is surprising. The mucolytic action of the hypochlorite effectively liberates the micro organism from the surrounding sample matrix and then also extracts the desired antigens and simultaneously reduces the non-specific binding that can be associated with the mucous in a sample. Description of a kit containing these reagents is presented in Example 4. The mucolytic effect of hypochlorite is also observed in the hypochlorite/nitrous method.

In a preferred embodiment, the sample is reacted with hypochlorite and sodium nitrite in the presence of a chelating agent and a disulfide reducing agent. Hypochlorite can be used alone.

In preferred embodiments of the extraction methods and methods for lysing mucous in a sample, the antigen is selected from the group consisting of carbohydrates, proteins, lipoproteins, lipopolysaccharides, polysaccharides, nucleic acids, carbohydrates complexed with proteins, lipids, DNA, and RNA; the organism is of the species *Streptococcus*, most preferably the Group B Streptococcus, Group G Streptococcus, Group A Streptococcus or Group F Streptococcus.

In a sixth aspect, the invention features a kit for the extraction of antigens from micro organisms including one or more of the following components: extraction tubes, extraction tubes containing dried sodium nitrite, an aliquot of acetic acid solution, an aliquot of strong base solution, an aliquot of hypochlorite solution, and an aliquot of neutralizing buffer.

In a seventh aspect, the invention features a method for detection of antigens extracted from microorganisms contained in a sample. The method includes contacting the sample with reagents which generate nitrous acid for a period of time sufficient for the nitrous to extract the antigen, further reacting the sample with base for a period of time sufficient to increase exposure of the antigen, neutralizing the sample, contacting the sample with a test surface which specifically binds the antigen, and detecting the binding of the antigen to the test surface by a suitable analytical method.

By "test surface which specifically binds the antigen" is meant a surface that can be used in an optical immunoassay detection method or a surface suited to another analytical method such as: antibody, nucleic acid, or antigen coated microtiter wells, test tubes, polystyrene beads, micro-particle beads, membranes or other surfaces known to those skilled in the art.

By "suitable analytical method" is meant an optical detection method; enzyme immunoassays in microtiter wells, test tubes, membranes, or on beads; radioimmunoassays; chemiluminiscent assays; fluorescent assays, agglutination assays, and other techniques as would be known to those skilled in the art. Suitable analytical methods include: diffraction methods, SPR, ellipsometry, thin film interference effects, spectrophotometry, reflectometry, changes in intensity or degree of polarization, scanning tunneling microscopy (STM), atomic force microscopy (AFM), total internal reflectance, interferometry, piezoelectric sensors, and other related optical and electrochemical methods.

In a preferred embodiment, the sample is contacted with a secondary label or signal generating component following the neutralization step.

A "secondary label" in an optical immunoassay, produces mass enhancement. This could include an enzyme labeled antibody in combination with a substrate for the enzyme which produces an insoluble or precipitating product. Or it could include materials which will bind the appropriate analyte via a specific secondary binding reagent adhered to a film forming latex. For other methods, the label is selected to match the analytical method. For example, a radiolabel is used in an RIA, an enzyme in combination with a chromogenic substrate in an EIA, a fluorescent label in an FIA or IFA, and others as are known to those skilled in the art. The secondary label is directly or indirectly responsible for the generation of a signal. In general, the secondary label is attached to a binding agent specific to the analyte of interest.

By "signal generating component" is meant a component that allows for the production of a signal detectable by a suitable analytical method. The secondary label may intrinsically generate signal as in an RIA, or the secondary label may act on another material to generate signal as in an EIA where an enzyme converts a substrate (no signal) to a product (signal). The enzyme converts a chromophore to a form with a higher extinction coefficient at a specific wavelength. In this example, signal is a visible color change or a spectrophotometric measurement. The signal measured is a function of the detection method used and should be clear to one skilled in the art.

In an eighth aspect, the invention features a method for detection of antigens extracted from microorganisms contained in a sample comprising the steps of reacting the sample with hypochlorite for a period of time sufficient to extract the antigen, neutralizing the sample, contacting the sample with a test surface which specifically binds the antigen, and detecting the binding of the antigen by a suitable analytical method.

In a preferred embodiment, the sample is reacted with reagents which generate nitrous acid following the hypochlorite contacting step.

In another preferred embodiment, the analytical method is selected from the group consisting of ellipsometry, comparison ellipsometry, spectrophotometry, reflectometry, thin film interference effects, surface plasmon resonance, total internal reflection, interferometers, attenuated total reflectance, piezoelectric sensors, frustrated internal reflection, changes in the rotation of polarization or changes in the intensity of polarized light, waveguide sensors, AFM, STM, and immunoassays utilizing radioactive, enzymatic, metallic particles, fluorescent, or chemiluminescent labels, or agglutination.

In a ninth aspect, the invention features an assay kit for the detection of antigens extracted from micro organisms utilizing the methods of the invention and comprising one or more of the following components:
extraction tubes, extraction tubes containing dried sodium nitrite, an aliquot of hypochlorite solution, an aliquot of a solution of strong base, an aliquot of acetic acid solution, an aliquot of a neutralizing buffer, an aliquot of secondary label, an aliquot of precipitating substrate, an aliquot of wash solution, sample transfer pipettes, and a test surface.

By "precipitating substrate" is meant a substrate capable of interacting with a mass enhancement reagent or secondary label to produce an insoluble precipitating product.

By "wash solution" is meant water, a buffered solution, a detergent containing solution, or other such reagent.

In a preferred embodiment, the hypochlorite is produced by dissolving a solid hypochlorite salt to the desired final concentration.

BRIEF DESCRIPTION OF THE FIGURES

The drawings will first briefly be described.
DRAWINGS

DESCRIPTION OF THE PREFERRED EMBODIMENTS

Figure 1:
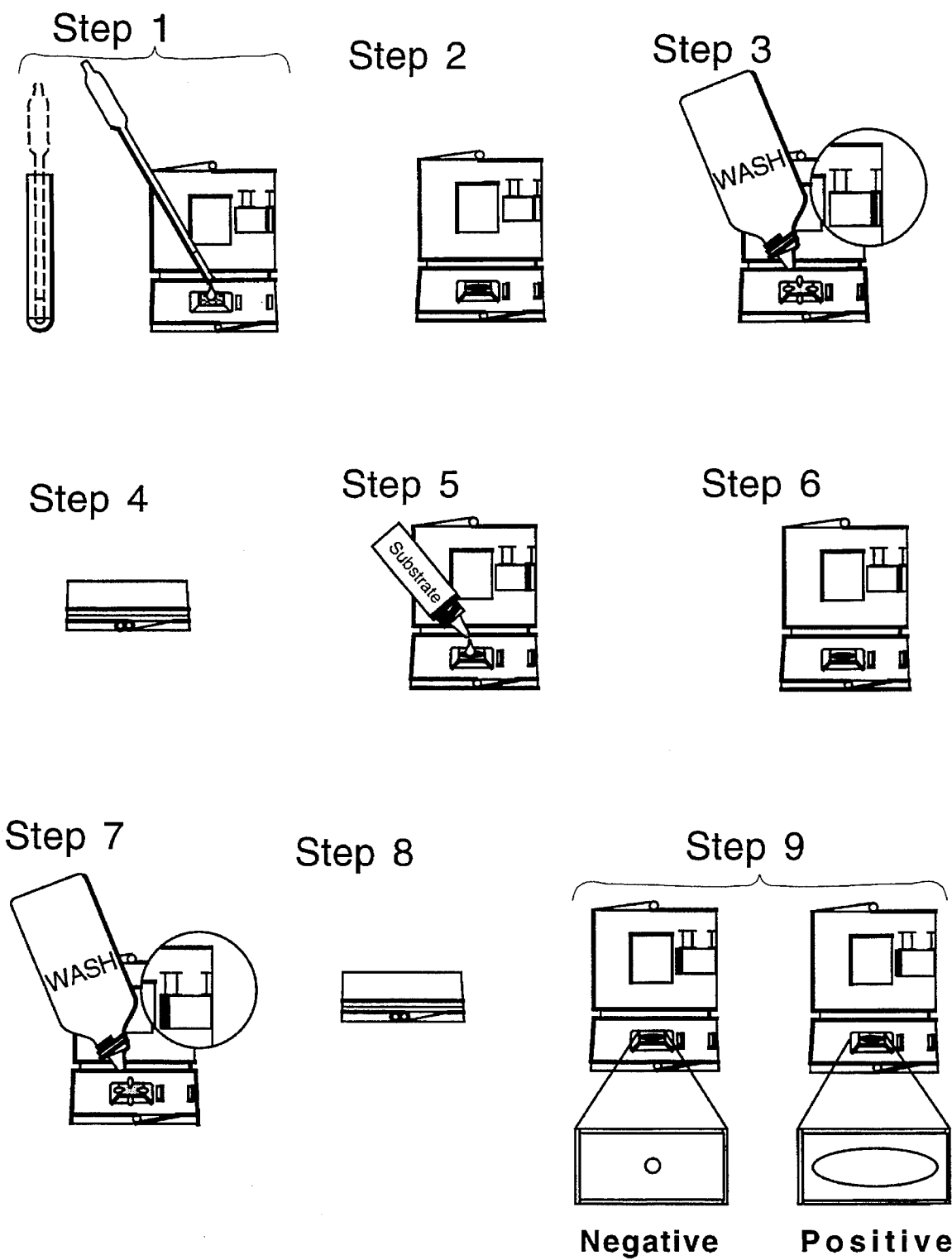
FIG. 1 is a diagram representation showing method steps for use of the single test device.

The following examples are for further illustrating the various aspects and embodiments of the present invention and are in no way intended to be limiting in scope.

Three different optical immunoassay detection methods are used in the preferred embodiments of this invention. These methods are based on tile study of thin films. While these techniques are optimal, a variety of other methods may be useful with these extraction techniques. Selection of the appropriate test surface for the detection method employed should be obvious to anyone skilled in the art. For example, the diffraction assay method described by Gustafson in U.S. Pat. No. 4,876,208 or Nicoli in U.S. Pat. No. 4,647,544, or related methods would be a suitable detection method for this invention. The test surface utilized would contain the diffraction grating required to generate the appropriate signal. Other suitable detection methods are: surface plasmon resonance as described in U.S. Pat. Nos. 4,828,387 and 4,931,384 and other publications; the techniques of total internal reflection, interferometers, attenuated total reflectance, piezoelectric sensors, atomic force microscopy (AFM), scanning tunneling microscopy (STM), frustrated internal reflection, spectrophotometry, reflectometry, and a variety of waveguide sensors. Any type of immunoassay method would benefit from the antigen preparation methods of current invention.

One of the preferred optical methods relies on the interaction of white light with a series of thin films. In this case the thin films are used to create a destructive interference of white light thus leading to a visible color change on the surface of the optical substrate. The components of this optically active test surface include an optical substrate, an optical thin film, an attachment layer, and a receptive material. The optical substrate is selected to provide the desired level of reflectivity. This may be an intrinsic property of the substrate material or the substrate may be modified by additional layers to provide the desired properties. The optical thin film is selected based on the refractive indices of the thin film and the substrate and the desired color for the final color change. However, critical adjustments to the thickness of the optical thin film are made based on the type of attachment layer and receptive material used in the final assay, U.S. Ser. No. 08/075,952, supra. The attachment layer is selected, preferably, from a series of branched siloxanes. The receptive material is based on the antigen or analyte to be detected.

Silicon nitride, is one such optical thin film, and may be deposited onto the silicon wafers using a vapor deposition process well understood by those skilled in the semi-conductor or optics art. A variety of optical materials may be substituted for the silicon nitride layer and are described in U.S. Ser. No. 08/075,952 supra.

The other methods rely on the interaction of ellipsometrically or linearly polarized light with the thin films on the optical substrate. The selection of a substrate is based again on the desired reflectivity for the instrument to be used. The use of an optical thin film is optional in the instrumented detection of thin film changes. But the attachment layer and receptive material used are the same as for the first optical method. Reacted test surfaces are then examined for a change in light intensity of the reacted zone relative to the unreacted zone. This change in light intensity may represent a shift in wavelength, the degree or intensity of ellipticity, the degree or intensity of polarization, the degree or intensity of elliptically polarized light, or the degree or intensity of linearly polarized light. For a more detailed description see U.S. Ser. No. 08/075,952, supra.

The attachment layer is preferably selected from a series of reagents consisting of branch structured siloxanes, dendrimers, star polymers, molecular self-assembling polymers, polymeric siloxanes, or film forming latexes. A preferred attachment layer is a T-structured branched siloxane and is produced by a spin coating technique. A 1:300 (v/v) dilution of the T-polymer (T-Polymer-Aminoalkyl T-structure branch point polydimethyl siloxane, Petrarch, Bristol, Pa.) may be prepared in 2-methyl-2-butanol. The attachment layer is applied to the silicon wafer by a spin coating method and is cured for 24 hours at 140° C. prior to use. A final layer of 100–160 Å is generally preferred. For spin coating, a 300 microliter sample of this solution is placed on a 100 mm virgin test silicon wafer by micropipette, although automated aerosol or spray delivery systems are equally useful, while the wafer is spinning at 7,000 rpm on a photoresist spincoater. Spin coating can rapidly process a large number of substrates. The process is also readily automated.

Receptive materials are coated onto the attachment layers applied to the optical substrate from a buffered solution. Buffers covering the pH range of 5.0 to 9.0 have been demonstrated to provide an effective receptive layer coating. A wide variety of buffer formulations may be used. Receptive materials can be coated onto the attachment layer by incubation at a wide range of temperatures and for varying periods of time. One such receptive layer, and the one to be preferred for an immunoassay, is an antibody. Antibody is then stabilized with a protective protein coating.

Antibody coated test surfaces may be placed in single test devices prior to assay. Use of the assay device is described below. U.S. Ser. No. 08/075,952, supra.

Once antigen is extracted it may be necessary to react the immobilized antigen with a secondary label to facilitate detection. In the thin film optical methods, this means enhancing the mass generated on the surface as a function of the amount of analyte on the surface. In a preferred embodiment, extracted antigen is mixed 5:1 (sample:secondary label) with a 1:100 dilution of the secondary label preparation containing 50 mM MOPSO, pH 7.0, 3% alkaline treated casein, 0.2% TWEEN20™ detergent, and 0.5% PROCLIN300™ preservative. The exact dilution used varies with the secondary label preparation and the detection method. A range of sample to secondary label ratios are acceptable. The sample/secondary label mixture is incubated for 5 minutes at room temperature, then 20 µl of the mixture applied to the test device and incubated for 5 minutes at room temperature; or alternatively 10 minutes directly on the surface. Incubation times may vary with the concentration and ratio of the secondary label.

For mass enhancement of an optical immunoassay, an antibody preparation may be conjugated to HRP, horseradish peroxidase, using the Nakane periodate method. An enzyme in combination with a precipitating substrate will form an additional layer of material which enhances the thin film effect being measured. Secondary binding reagents may be combined with other types of materials which introduce additional mass into the thin film formed on the surface as a function of analyte concentration. U.S. Ser. No. 08/075, 952, supra.

Referring to FIG. 1, there is shown a method by which a single test device is used. Specifically, in step 1 a sample is obtained and applied to the test surface. Such application is performed with the device open. In step 2 the sample is allowed to incubate so that any analyte present in the sample reacts with the antibody layer. At step 3 the sample is washed from the test surface and the excess liquid allowed to flow into the filter below the pyramid holding the test device. At this stage the position of the upper filter material is at I. In step 4 the device is closed and latched so that the filter may blot the test surface. In step 5 a drop of TMB precipitating substrate is applied to the device and allowed to incubate (step 6) for 5–10 minutes and then again rinsed (step 7) as above. At this point, the upper filter material is moved from position I to II, and the device again closed to allow the test surface to be dried (step 8). At this point, the device is again opened and the result read (step 9).

When instrumented results are desired, the wash dry protocol is accomplished by rinsing the test surface under a stream of deionized water and drying under a stream of nitrogen.

EXAMPLE 1

Three extraction methods were compared to a standard nitrous method for their ability to free group specific polysaccharide from GBS. Relative efficiencies of the extraction techniques were determined using a visual, optical immunoassay based on the interference of light. Ellipsometric analysis of these surfaces is also possible. For all results described here, CDC strain number CDCSS893 of GBS was used.

The polyclonal antibody preparation was used to coat the T-polymer coated, 495 Å $Si_3N_4$ optical thin film, silicon wafer was an affinity and protein G purified IgG fraction. The immunogen used to produce antibodies was inactivated whole cells of GBS. The coating antibody concentration was in the range of 100 to 500 µg of antibody per 100 mm wafer. Wafers were coated at 2–8 degrees C. for 2 to 48 hours. The preferred antibody coating concentration was 200 µg per 100 mm wafer in a buffer containing 0.1M HEPES, pH 8.0.

To evaluate the efficacy of each of the extraction methods, clinically negative vaginal swabs were utilized. Some of these swabs were spiked with GBS cells and the recovery of GBS was evaluated in a clinically relevant sample matrix, i.e., a sample containing mucous, blood, etc. Vaginal swabs collected during pregnancy frequently are contaminated with mucous, blood, and a wide range of micro organisms. Thus, of particular concern was the ability of the extraction reagent to extract the relevant antigens while also serving as a mucolytic agent. A mucolytic effect or other mechanism for the disruption of the sample matrix reduces or eliminates non-specific binding and should also increase the recovery of extracted antigens. Similar analytical sensitivity studies were performed on clean, sterile swabs without matrix. Results were identical to those described in the study with a clinically relevant sample matrix.

A comparison of a standard nitrous acid extraction method was done relative to base or hypochlorite modifications of that technique. In addition a hypochlorite only extraction method was examined. The results are shown in Table 1. The base modified protocol was examined at two levels of acetic acid; 0.25M and 1.6M.

As previously described clinically negative vaginal swabs were spiked with the designated amount of GBS cells and then the swabs processed through the extraction protocol.

In the standard nitrous acid method, a mixture of 120 µl of 0.25M acetic acid and 100 µl of 2.3M sodium nitrite (previously dried into the extraction tube) is used to generate nitrous acid. The acetic acid is found to effectively extract antigen in the range of 0.1M to 1.0M. Antigen is extracted from the organism for 5 minutes, although a range from instantaneous to 30 minutes is acceptable. The solution is neutralized using 120 µl of a buffer containing 1.5M MOPSO, pH 7.3, 0.2% TWEEN20™ detergent, 15% bovine serum, 0.5% PROCLIN300™ preservative, AND 20 mM EGTA. A final pH range of 7.0 to 7.5 is desired.

Base modification of this standard nitrous acid extraction technique consists of a mixture of 120 μl of 0.25M or 1.6M acetic acid, depending on the experiment, containing 10 mM EDTA and 5 mM DTT, and 100 μl of 2.3M sodium nitrite (previously dried into the extraction tube) which is used to generate nitrous acid. The acetic acid extracts antigen in the range of 0.25M to 1.0M for this modification of the nitrous technique. Antigen is extracted from the organism for 5 minutes. The pH of the acid step should be in the range of 4.0 to 5.0. A range from instantaneous to 10 minutes is acceptable. Additional extraction is observed when 100 μl of 2N NaOH is added and allowed to incubate for 1 minute. A range of 2N to 6N is acceptable for the NaOH, while the incubation period can be 0.5 to 10 minutes. The pH of the base step should be in the range of 12–14. The solution is μl of the mixture applied to the text device and incubated for 5 minutes at room temperature; or alternatively 10 minutes on the surface. Incubation times may vary with the concentration of the conjugate and the sample: conjugate ratio.

When the visual interference test surface is used (see FIG. 1), the sample is rinsed from the surface by a stream of deionized water and the lid of the test device is closed. This brings an absorbent material into contact with surface and dries the test surface. The device is re-opened to expose the test surface. A precipitating substrate is then applied to the test surface and incubated for 10 minutes for room temperature. The slide in the lid of the device is moved to provide dry absorbent material, and once the substrate is rinsed from the test surface the lid is closed to repeat the drying process. The device is opened and the result interpreted.

TABLE 1

| EXTRACTION PROTOCOL | $3 \times 10^{6}$* | $3 \times 10^{5}$* | $3 \times 10^{4}$* | $1 \times 10^{4}$* | 0 |
|---|---|---|---|---|---|
| STANDARD NITROUS | ++ | + | +/− | +/− | +/− |
| BASE MODIFIED[a] | ++ | ++ | + | +/− | − |
| BASE MODIFIED[b] | +++ | ++ | + | + | − |
| HYPOCHLORITE/ NITROUS ACID | +++ | ++ | + | + | − |
| HYPOCHLORITE ALONE | ++ | ++ | + | + | − |

*Number of cells per assay.
[a]No incubation period followed the addition of base. A high concentration of acetic acid (1.6M) was used in the extraction protocol.
[b]No incubation period followed the addition of base. A low concentration of acetic acid (0.25M) was used in the extraction protocol.

neutralized using 250 μl of a buffer containing 2.0M MOPSO, pH 6.0, 0.2% TWEEN20™ detergent, 15% bovine serum, 0.5% PROCLIN300™ preservative, and 20 mM EGTA. A final pH range of 6.0 to 7.5 is desired.

The hypochlorite extraction technique utilizes 120 μl of 10% available hypochlorite solution, in the form of sodium hypochlorite. This method performs optimally when a greater than 6% solution of hypochlorite is used. Antigen is extracted from the organism for 5 minutes. A range from instantaneous to 30 minutes is acceptable. The hypochlorite solution is neutralized after the incubation step with 120 ul of 1.5 M MOPSO, pH 7.3, 0.2% TWEEN20™ detergent, 15% bovine serum, 0.5% PROCLIN300™ preservative, and 20 mM EGTA. When the hypochlorite is combined with sodium nitrite, 100 ul of 2.3M sodium nitrite (dried into the extraction tube) is used.

In the hypochlorite/nitrous acid extraction method, extraction is continued by the addition of 120 μl of 0.5M acetic acid containing 10 mM EDTA and 5 mM DTT to the hypochlorite sodium nitrite solution and incubation is for 5 minutes. The acetic acid is found to extract the GBS antigen in the range of 0.25M to 2.0M for this modification of the nitrous technique. The solution is neutralized using 300 μl (with 2M acetic acid) of a buffer containing 1.5M MOPSO, pH 7.0, 0.2% TWEEN20™ detergent, 15% bovine serum, 0.5% PROCLIN300™ preservative, and 20 mM EGTA. A final pH range of 6.0 to 7.5 is desired.

The extracted antigen is mixed 5:1 (sample:conjugate) with a 1:100 dilution of the conjugate preparation containing 50 mM MOPSO, pH 7.0, 3% alkaline treated casein, 0.2% TWEEN20™ detergent, and 0.5% PROCLIN300™ preservative. The exact dilution of the conjugate preparation used varies with the conjugate preparation. A range of sample to conjugate ratios are acceptable. The sample/conjugate mixture is incubated for 5 minutes at room temperature, then 20

The analytical sensitivity studies examining the effect of a strong base on the continued extraction of GBS indicated that there was increased recovery of the GBS specific antigen relative to a standard nitrous acid extraction. In addition, the base modified nitrous extraction seems to have a mucolytic effect on the sample matrix. Thus, the base modified protocol was overall more effective than the standard nitrous protocol. Some loss in signal intensity was observed when the base modification was combined with a very strong nitrous acid extraction (use of 1.6M acetic acid), and neutralization of the extract was more difficult to achieve. Thus, acetic acid levels of less than 0.75M when combined with the base modification are preferred. The lower level of acid used was also more tolerant to variations in the amount of added neutralizer or excess acid. The results in Table 1 indicated that the observed enhancement in antigen detection was due to the base modified protocol and not to a higher level of nitrous acid. It was also demonstrated that the base effect occurs rapidly. No incubation period at an elevated pH was required to elicit the effect.

The hypochlorite/nitrous extraction protocol provided the best extraction efficiency. The analytical sensitivity was better than for the nitrous alone. The biggest advantage to the technique was the improvement of the antigen extraction efficiency in a clinically relevant sample matrix. The clinically negative sample swabs provided clean negative responses, i.e., reduced non-specific binding. The hypochlorite/nitrous protocol was more tolerant than the base modified protocol to the variation of excess reagent volumes. Thus, the method was more robust. Hypochlorite alone also showed enhanced analytical sensitivity relative to the nitrous acid method and exhibited the mucolytic effect desired.

Both of these methods, base modified and hypochlorite/nitrous, extract Group A Streptococci (GAS) antigen, Group B Streptococci (GBS) antigen, Group F Streptococci antigen, and Group G Streptococci antigen. These extraction techniques also readily extract the GBS antigen from colonies which are non-beta hemolytic and thus are not readily identified by standard culture techniques.

EXAMPLE 2

Hypochlorite Extraction of Streptococcal Organisms

Commercially available serotyping reagents for *Streptococci* Groups A, B, C, F, and G were used to evaluate the utility of the hypochlorite/nitrous reagent to extract the group specific polysaccharide antigens. Trypticase soy agar plates containing 5% sheep blood were used to prepare pure, isolated colonies of each organism. A wooden sampling apparatus was used to sample several colonies. The swabs were extracted with the hypochlorite/nitrous protocol described in Example 1. Extracted antigens where assayed with the appropriate serotyping reagent according to the manufacturer's protocol.

| ORGANISM | ATCC STRAIN # | AGGLUTINATION OBSERVED |
| --- | --- | --- |
| B | 12386 | ++++ |
| F | 12393 | +++ |
| G | 12394 | ++ |
| A | 19615 | + |
| C | 12388 | − |

The hypochlorite/nitrous acid protocol described in Example 1 was optimized for the extraction of Group B specific polysaccharide. The optimization process involved the examination of varying acetic acid, hypochlorite, $NaNO_2$, and neutralizer concentrations (and pH for the neutralizer). In addition, the order of reagent addition, and incubation times for each step were examined. Generally, one reagent is varied while the others are held constant. Swabs spiked with a known amount of GBS cells were processed through a large number of these various protocols and then assayed under identical conditions with the interference test surface. Results were compared to determine the effect on the negative samples, weak positives, and strong positives. Once broad ranges for all the reagents were selected, additional experiments were used to finalize the reagent composition. Thus the conditions are fairly specific for GBS. A similar process could be followed for any organism. These types of optimization studies are well understood by those skilled in this type of assay development. Without any optimization for the other organisms, extraction of the group specific polysaccharide is observed. Conditions appear to be well suited to the extraction of Groups B and F.

EXAMPLE 3

Hypochlorite/Hyponitrous Acid Extraction of GBS Combined with A Membrane EIA Assay A commercially available GBS antigen test was used in combination with the hypochlorite/nitrous acid extraction protocol of Example 1. The membrane assay was performed according to manufacturer's protocol. A cell suspension of GBS was prepared in 0.85% sterile saline to a cell density of $3 \times 10^8$ cells/ml. Cell dilutions were made by serial dilution in sterile saline. A 100 µl aliquot was added to extraction tubes and then extracted as described. This extraction method was compared to the manufacturer's recommended extraction protocol, which is based on nitrous acid.

| TEST METHOD | CELL CONC.* | MANU- FACTURER'S EXTRACTION | HYPO- CHLORITE EXTRACTION |
| --- | --- | --- | --- |
| MEMBRANE EIA | $3 \times 10^6$ | ++ | +++ |
| | $3 \times 10^5$ | + | + |
| | $3 \times 10^4$ | − | − |

*Number of cells per assay.

Without optimization to the membrane assay system, the hypochlorite/nitrous acid extraction protocol increases the signal observed for a cell concentration of $3 \times 10^6$.

EXAMPLE 4

Comparison of the Analytical Sensitivity of an Optical Interference GBS Assay including the Hypochlorite/nitrous Extraction Protocol to Commercially available GBS Assays.

The Strep B OIA™ tests kit was compared with commercially available GBS assay kits for analytical sensitivity.

The Strep B OIA™ tests kit for the assay of vaginal swabs for the detection of GBS consists of the following components:

extraction tubes containing dried sodium nitrite, acetic acid in a dropper bottle, hypochlorite solution in a dropper bottle, neutralizer in a dropper bottle, a dropper bottle containing secondary label, a dropper bottle of precipitating substrate, a bottle of wash solution, disposable transfer pipettes, and a single use assay device containing a test surface with a silicon nitride coated silicon wafer.

Strep B OIA™ tests Kit Components:

Extraction tubes contain dried sodium nitrite ($NaNO_2$) 2.3M; 100 µl.

Extraction Reagent 1A: Contains sodium hypochlorite (<15% available chlorine).

Extraction Reagent 1B: Contains 0.5M acetic acid, pH 3.

Reagent 2 (Neutralization Reagent): Contains 1.5M MOPSO, 20 mM EGTA, 0.2% TWEEN20™, (15% bovine serum) and 0.5% PROCLIN300™ preservative.

Reagent 3 (Secondary Label): Contains buffered antigroup B streptococcus antibody (rabbit) conjugated to horseradish peroxidase (HRP). 1:100 Ab dilution in 50 mM MOPSO, pH 7.0, 3% alkaline treated casein, 0.2% TWEEN20™, 0.5% PROCLIN300™ preservative.

Reagent 4 (Wash Solution): $H_2O$ w 0.1% PROCLIN300™ preservative.

Reagent 5 (Precipitating Substrate): Tetramethylbenzidine (TMB) and hydrogen peroxide ($H_2O_2$).

Test Devices: Surface coated with anti-group B streptococcus antibody (rabbit).

Positive Control: Purified group B Streptococcal antigen.

Transfer pipettes.

TEST PROCEDURE

1. Remove reagent(s) from refrigerated storage and allow to warm to room temperature (18°–30°). Store Reagent 4 at room temperature (18°–30° C.) after opening. Test devices may be stored at room temperature or refrigerated at 2°–30° C.

2. Remove an Extraction Tube containing dry reagent from the kit and place it upright in a rack or holder.

3. Label Test Devices with appropriate patient information. Place Test Devices on a level surface while the assay is being performed.

4. Add 3 drops of Reagent 1A into the Extraction Tube and shake it gently to dissolve the dry reagent in the bottom.

5. Within 1 minute, place Positive Control or a swab containing a specimen into the tube. Mix the solution with the swab so that the liquid is moved in and out of the fiber tip. Allow the swab to stand in the extraction solution for a minimum of 3 minutes and not more than 5 minutes.

6. Hold the swab shaft to the side and add 3 drops of Reagent 1B directly into the Extraction Tube. Use the swab to mix the reagent with the extract. Allow the swab to stand in the extraction solution for a minimum of 3 minutes and not more than 5 minutes.

7. Hold the swab shaft to the side and add 3 drops of Reagent 2 directly into the Extraction Tube. Use the swab to mix the reagent with the extract.

8. Squeeze the sides of the Extraction Tube as the swab is withdrawn, expressing as much fluid as possible into the tube. Discard the swab and retain the contents of the tube. Retain as much fluid from the swab as possible.

Note: If insufficient sample volume is obtained when squeezing fluid from the swab, 1 or 2 drops of additional Reagent 2 may be added to the Extraction Tube. Mix well with the swab and repeat Step 8.

9. Add 1 drop of Reagent 3 to the extract and mix thoroughly either with a vortex or by shaking tube. Do not let stand more than 5 minutes.

10. Use a clean Transfer Pipette to place 1 drop (0.05 ml) of the solution directly onto the center of the surface of the corresponding Test Device. Do not cover the entire surface of the Test Device.

11. Wait for 10 minutes.

12. Wash the test surface vigorously with a hard squirt of Reagent 4 Wash Solution taking care not to exceed the capacity of the absorbent material surrounding the device. A vigorous wash of 3–4 seconds duration is very important.

Note: A vigorous wash is very important to insure a complete and thorough rinsing of the test surface prior to the next procedure step. Insufficient washing of the test surface may leave debris which may result in a faint ring surrounding the procedure control dot. While this ring effect would not be interpreted as a positive result due to the lack of color shading within the ring area, vigorous washing will obtain a clean test surface.

13. Confirm that the blotting device is in position #1. Close the test device by applying pressure at the corners. Leave closed for 10 seconds to remove residual moisture from the surface.

Note: Blot with a clean surface each time blotting is necessary. Blotter should be in position I when blotting for the first time. If in position II, move to position I for the second blot. Repeated blotting in the same position may compromise test results.

14. Open the lid and apply 1 drop of Reagent 5 directly onto the center of the test surface of the Test Device and let stand for 10 minutes.

Note: If placement of the first drop was not directly onto the center of the Test Device, place the Reagent 5 drop directly over the area of the first drop.

15. Repeat Step No. 12, washing the test surface vigorously with a hard squirt of Reagent 4 Wash Solution. See Procedure Note in Step No. 12.

16. Move the blotter in the lid of the Test Device to position #2. Close the test device by applying pressure at the corners. Leave closed for 10 seconds to remove residual moisture from the surface. Open the lid and examine the test surface for a color change.

INTERPRETATION OF TEST RESULTS

Upon completion of the each test, the test surface should be examined under a bright light source. The light must be reflected off the test surface to observe the test results.

An internal procedural control is present on each test surface. It appears as a small blue/purple dot in the center of the test surface upon completion of each test. A negative test result will show only the internal procedural control. A positive test result will show the internal control within the reaction circle. With very strong positive results, the internal control may be less apparent within the reaction circle.

POSITIVE OR WEAK POSITIVE RESULT:

Solid blue/purple colored reaction circle of any intensity appears in the center of the test surface.

NEGATIVE RESULT:

For a negative result, no solid blue/purple color over the entire test surface should be observe, only the small procedural control spot. An invalid result occurs when no procedural control spot is observed. Repeat the procedure following the instructions carefully.

The reacted test surface and the color change associated with a positive reaction will not deteriorate over time. Therefore, the Test Device may be considered a permanent record. If a Test Device is to be saved for reference, the blotting material in the lid should be removed and disposed of in a biohazard container. The device should be closed for storage.

Other kits compared to the optical assay system were a DNA probe method, a membrane EIA method, and a latex agglutination method. All tests were performed according to the manufacturer's protocol.

| TEST METHOD | ANALYTICAL SENSITIVITY |
| --- | --- |
| OIA$^{tm}$ tests | $5 \times 10^3$ CFU/assay |
| DNA PROBE | $5 \times 10^4$ CFU/assay |
| MEMBRANE EIA | $5 \times 10^5$ CFU/assay |
| LATEX | $3 \times 10^6$ CFU/assay |

The OIA method is between 10 and 1000 fold more sensitivity based on analytical sensitivity than any commercially available GBS assay.

Other embodiments are within the following claims.

What is claimed is:

1. Method for extracting an antigen from a micro organism of the genus streptococcus contained in a sample comprising the steps of:

first contacting the sample with reagents which generate nitrous acid for a period of time sufficient to allow the nitrous acid to extract said antigen so as to result in a sample comprising extracted antigen, second contacting the sample comprising extracted antigen with base for a period of time sufficient to increase the exposure of the antigen so as to result in a sample comprising antigen of increased exposure, and neutralizing the sample comprising antigen of increased exposure.

2. Method for extracting an antigen from a micro organism of the genus streptococcus contained in a sample and lysing mucus in the sample, comprising the steps of:

first contacting the sample with reagents which generate nitrous acid for a period of time sufficient to allow the nitrous acid to extract the antigen so as to result in a sample comprising extracted antigen;

second contacting the sample comprising extracted antigen with base for a period of time sufficient to increase the exposure of the antigen and to lyse mucus in the sample comprising extracted antigen, so as to result in a sample comprising antigen of increased exposure and lysed mucus; and neutralizing the sample comprising antigen of increased exposure and lysed mucus.

3. The method of claim 2, wherein said sample is reacted with reagents which generate nitrous acid in the presence of a chelating agent and a disulfide bond reducing agent.

4. The method of claim 3, wherein said chelating agent is EDTA or EGTA present in an amount from 0.1 to 100 mM and said disulfide bond reducing agent is dithiothreitol present in an amount from 0.1 to 100 mM.

5. The method of claim 1, wherein said reagents which generate nitrous acid are acetic acid present in an amount from 0.25M to 1.0M and sodium nitrite present in an amount from 0.5 to 0.25M, said first contacting is from 0.5 to 10 minutes, said second contacting is for a period of time from 2 to 10 minutes, said base consists of NaOH present in an amount from 2N to 6N, and said neutralizing is achieved by adding a buffer containing MOPSO at pH 6.0 present in an amount from 1.0 to 2.5M.

6. Method for extracting an antigen from a micro organism of the genus streptococcus contained in a sample, comprising the steps of:

contacting the sample with hypochlorite, and sodium nitrite for a period of time sufficient to extract the antigen so as to result in a sample comprising extracted antigen, and neutralizing said sample comprising extracted antigen.

7. Method for extracting an antigen from a micro organism of the genus streptococcus contained in a sample comprising the steps of:

first contacting the sample with hypochlorite and sodium nitrite;

incubating for a period of time sufficient to allow the hypochlorite to extract the antigen so as to result in a sample comprising extracted antigen;

contacting the sample comprising extracted antigen with reagents which generate nitrous acid for a period of time sufficient to increase the exposure of the antigen so as to result in a sample comprising antigen of increased exposure; and neutralizing said sample comprising antigen of increased exposure.

8. Method for lysing mucus contained in a sample comprising an antigen from a microorganism of the genus streptococcus, comprising the steps of:

contacting the sample with hypochlorite and sodium nitrite for a period of time sufficient to lyse mucus in the sample so as to result in a sample comprising lysed mucus; and neutralizing the sample comprising lysed mucus.

9. The method of claim 8, wherein said sample is reacted with hypochlorite and sodium nitrite in the presence of a chelating agent: and a disulfide bond reducing agent.

10. The method of claim 9, wherein said chelating agent is EDTA or EGTA present in an ,amount from 0.1 to 100 mM and said disulfide bond reducing agent is dithiothreitol present in an amount from 0.1 to 100 mM.

11. The method of claims 6, 7, or 8, wherein said hypochlorite is present in an amount from 0.1% to 10%, said sodium nitrite is present in an amount from 0.5 to 2.5M, said first contacting is for a period of time from 2 to 30 minutes, and said neutralizing is achieved by adding a buffer containing MOPSO at pH 7.0 present in an amount from 1.0 to 2.5M.

12. The method of claim 7, wherein said reagents which generate nitrous acid comprise acetic acid present in an amount from 0.25 to 2.0M.

13. The method of claims 1, 2, 6, 7, or 8, wherein said antigen is selected from the group consisting of carbohydrates, proteins, lipoproteins, lipopolysaccharides, polysaccharides, nucleic acids, lipids, lipids, DNA, RNA, and carbohydrates complexed with proteins.

14. The method of any of claims 1, 2, 6, 7 or 8, wherein said micro organism is Group B Streptococcus.

15. The method of any of claim 1, 2, 6, 7, or 8, wherein said micro organism is Group G Streptococcus.

16. The method of any of claims 1, 2, 6, 7, or 8, wherein said micro organism is Group A Streptococcus.

17. The method of any of claims 1, 2, 6, 7, or 8, wherein said micro organisms Group F Streptococcus.

18. Kit for the extraction of antigens from micro organisms of the genus streptococcus comprising;

extraction tubes containing dried sodium nitrite;

an aliquot of acetic acid solution;

an aliquot of strong base solution; and an aliquot of neutralizing buffer.

19. Kit for the extraction of antigens from micro organisms of the genus streptococcus comprising;

extraction tubes containing sodium nitrite;

an aliquot of hypochlorite solution; and an aliquot of a neutralizing buffer.

20. The kit of claim 21, wherein an aliquot of acetic acid solution is also included.

21. The kit of claim 18, 19, or 20, wherein EDTA and dithiothreitol are included.

22. Method for detection of an antigen extracted from a micro organism of the genus streptococcus contained in a sample comprising the steps of:

first contacting the sample with reagents which generate nitrous acid for a period of time sufficient to allow the nitrous acid to extract the antigen so as to result in a sample comprising extracted antigen;

second contacting the sample comprising extracted antigen with base for a period of time sufficient to increase exposure of the antigen so as to result in a sample with antigen of increased exposure;

neutralizing the sample comprising antigen of increased exposure so as to result in a neutralized sample;

third contacting the neutralized sample with a test surface which specifically binds said antigen; and detecting the binding of said antigen to said test surface by a suitable analytical method.

23. Method for detection of an antigen extracted from a micro organism of the genus streptococcus contained in a sample comprising the step of:

first contacting the sample with hypochlorite for a period of time sufficient to extract the antigen so as to result in a sample comprising extracted antigen, neutralizing the sample comprising extracted antigen so as to result in a neutralized sample, second contacting the neutralized sample with a test surface which specifically binds said antigen, and detecting the binding of said antigen by a suitable analytical method.

24. The method of claim 22 or 23, wherein said neutralized sample is contacted with a secondary label or signal generating component.

25. The method of claim 23, wherein said sample comprising extracted antigen is contacted with reagents which generate nitrous acid for a period of time sufficient to increase the exposure of the antigen prior to neutralization.

26. The method of claims 22, 23 or 25, wherein said analytical method is selected from the group consisting of:

ellipsometry, comparison ellipsometry, thin film interference effects, surface plasmon resonance, total internal reflection, spectrophotometry, reflectometry, interferometers, attenuated total reflectance, piezoelectric sensors, frustrated internal reflection, changes in the rotation of polarization or changes in the intensity of polarized light, waveguide sensors, AFM, STM, particle based agglutination, and immunoassays utilizing labels such as enzymes, radioactive isotopes, metallic particles, fluorphors, or chemiluminescent materials.

27. The kit of claims 25 or 26, further comprising an aliquot of wash solution and sample transfer pipettes.

28. Assay kit for the detection of antigens extracted from micro organisms of the genus streptococcus comprising:

extraction tubes containing dried sodium nitrite;

an aliquot of hypochlorite solution;

an aliquot of acetic acid solution, an aliquot of a neutralizing buffer;

an aliquot of secondary label;

an aliquot of precipitating substrate; and a test surface.

29. Assay kit for the detection of antigens extracted from micro organisms of the genus streptococcus comprising:

extraction tubes containing dried sodium nitrite;

an aliquot of acetic acid solution, an aliquot of a neutralizing buffer;

an aliquot of secondary label;

an aliquot of precipitating substrate;

an aliquot of a solution of strong base; and a test surface.

30. The kit of claim 28, wherein said hypochlorite solution is produced by dissolving a solid hypochlorite salt to the desired final concentration.

31. Method for extracting an antigen from a micro organism of the genus streptococcus contained in a sample, comprising the steps of:

contacting the sample with hypochlorite for a period of time sufficient to extract the antigen so as to result in a sample comprising extracted antigen; and neutralizing said sample comprising extracted antigen.

32. Method for lysing mucus contained in a sample comprising an antigen from a micro organism of the genus streptococcus, comprising the steps of:

contacting the sample with hypochlorite for a period of time sufficient to lyse mucus in the sample so as to result in a sample comprising lysed mucus; and neutralizing the sample comprising lysed mucus.

33. The method of claim 32, wherein said sample is contacted with hypochlorite in the presence of a chelating agent and a disulfide bond reducing agent.

34. The method of claim 33, wherein said chelating agent is EDTA or EGTA present in an amount from 0.1 to 100 mM and said disulfide bond reducing agent is dithiothreitol present in an amount from 0.1 and 100 mM.

35. The method of claims 31 or 32, wherein said hypochlorite is present in an amount from 0.1% to 10%, said contacting is for a period of time from 2 to 30 minutes, and said neutralizing is achieved by adding a buffer containing MOPSO at pH 7.0 present in an amount from 1.0 to 2.5M.

36. The method of claim 31 or 32, wherein said antigen is selected from the group consisting of carbohydrates, proteins, lipoproteins, lipopolysaccharides, polysaccharides, nucleic acids, lipids, lipids, DNA, RNA, and carbohydrates complexed with proteins.

37. The method of any of claims 31 or 32, wherein said micro organism is Group B Streptococcus.

38. The method of any of claims 31 or 32, wherein said organism is Group G Streptococcus.

39. The method of any of claims 31 or 32, wherein said micro organism is Group A Streptococcus.

40. The method of any of claims 31 or 32, wherein said micro organism is Group F Streptococcus.

41. Kit for extraction of antigens from micro organisms of the genus streptococcus comprising:

an aliquot of hypochlorite solution; and an aliquot of a neutralizing buffer.

42. Assay kit for the detection of antigens extracted from micro organisms of the genus streptococcus comprising:

an aliquot of hypochlorite solution;

an aliquot of neutralizing buffer;

an aliquot of secondary label;

an aliquot of precipitating substrate;

an aliquot of wash solution; and a test surface.

43. The kit of claim 41 further comprising extraction tubes.

44. The kit of claim 42 further comprising extraction tubes and sample transfer pipettes.

* * * * *